United States Patent [19]

Nussenbaum

[11] Patent Number: 5,542,905
[45] Date of Patent: Aug. 6, 1996

[54] SWITCH MECHANISM FOR USE IN A LARYNGOSCOPE HANDLE

[75] Inventor: Joseph Nussenbaum, New York, N.Y.

[73] Assignee: Propper Manufacturing Co., Inc., Long Island City, N.Y.

[21] Appl. No.: 369,176

[22] Filed: Jan. 5, 1995

[51] Int. Cl.$^6$ ...................................................... A61B 1/26
[52] U.S. Cl. ........................... 600/191; 600/185; 600/193; 362/804; 362/32
[58] Field of Search ..................................... 600/185, 188, 600/193, 197, 199, 245, 249; 362/203, 204, 205, 206, 32, 804

[56] References Cited

U.S. PATENT DOCUMENTS

| | | | |
|---|---|---|---|
| 2,345,471 | 8/1943 | MacIntosh | 128/10 |
| 2,433,705 | 7/1946 | Palmeter | 128/10 |
| 3,638,644 | 2/1972 | Reick | 128/16 |
| 3,826,248 | 7/1974 | Gobels | 128/11 |
| 4,273,112 | 6/1981 | Heine et al. | 128/11 |
| 4,406,280 | 9/1983 | Upsher | 128/11 |
| 4,556,052 | 12/1985 | Müller | 128/11 |
| 4,557,256 | 12/1985 | Bauman | 128/11 |
| 4,565,187 | 1/1986 | Soloway | 128/11 |
| 4,570,614 | 2/1986 | Bauman | 128/11 |
| 5,060,633 | 10/1991 | Gibson | 128/11 |

*Primary Examiner*—Richard J. Apley
*Assistant Examiner*—Beverly M. Flanagan
*Attorney, Agent, or Firm*—Oppedahl & Larson

[57] ABSTRACT

A laryngoscope handle includes a switch assembly for creating an electrical circuit between a lamp and a battery when a laryngoscope blade attached to the handle is moved into a working position. The switch assembly is formed from: (1) a first sleeve in which the lamp is mounted, said first sleeve providing electrical contact between a side terminal of the lamp and the tubular base portion and leaving a base terminal of the lamp exposed, and said first sleeve being axially slidable within the handle; (2) a spring operative to press the first sleeve towards the head-end of the handle; (3) an electrically insulating barrel mounted within the handle between the first sleeve and the first end of the base portion, said electrically insulating barrel having an axial channel therethrough, said axial channel having a bottom region of greater cross section at a bottom end directed toward the first end of the tubular base portion and a top region of smaller cross section at a top end directed toward the head; (4) an electrically conductive sliding terminal, said sliding terminal being slidably disposed within the bottom region of the channel in the barrel; and (5) an electrically conductive plunger affixed to the sliding terminal and slidably disposed within the top region of the channel in the insulating barrel such that the sliding terminal and the plunger slide as a unit within the channel.

5 Claims, 5 Drawing Sheets

SWITCH MECHANISM FOR USE IN A LARYNGOSCOPE HANDLE

BACKGROUND OF THE INVENTION

This application relates to a switch mechanism for use in a laryngoscope handle.

In a known type of laryngoscope such as that disclosed in U.S. Pat. Nos. 4,556,052 and 4,273,112, which are incorporated herein by reference, the laryngoscope consists of a handle portion and a blade portion. The blade is movable between a rest or storage position in which it is substantially parallel to the handle, and a working position in which it is substantially perpendicular to the handle. In the working position, an optical fiber in the blade is aligned with a light source within the handle. Further placement of the blade into the working position activates a switch to energize the light source, such that light passes through the optical fiber to illuminate the area surrounding the distal end of the blade when the blade is in the working position.

Various designs have been disclosed for the switch which is activated when the laryngoscope blade is placed into the working position. One such design is shown in FIG. 4. As shown, a lamp 7 is mounted in a slidable mounting sleeve 21 and within a blade sleeve 8. A spring 101 presses the mounting sleeve 21 upward away from the a contact plunger 102. The contact plunger 102 is pressed upward by a second spring 103 relative to a contact terminal 104 which is screwed into insulating barrel 25. When the blade is swung into the working position, it presses on the blade sleeve 8, causing the blade sleeve 8, lamp 7 and mounting sleeve 21 to move in a downward direction against force of spring 101. This causes the base terminal 105 of the lamp 7 to come into contact with the contact plunger 102. The contact plunger 102 is in turn in electrical contact with the contact terminal 104 via the second spring 103.

While the switch mechanism shown in FIG. 4 works to turn the lamp on and off in response to the position of a blade attached to the handle, it is not without its drawbacks. In particular, the indirect contact between the contact plunger and the contact terminal can introduce problems if spring 103 breaks, or becomes disconnected from one of the two contact points, leading to intermittent flow of electrical current through the switch. Furthermore, the contact terminal 104 is always held in contact with the positive terminal of the upper most battery by the conical spring which acts as an electrical contact 3 at the base of the housing.

SUMMARY OF THE INVENTION

In accordance with the present invention, there is provided a laryngoscope handle comprising:

(a) a tubular base portion, (b) a first electrical contact disposed within and at a first end of the tubular base portion for making contact with a battery placed within said base portion;

(c) a head assembly attached to the tubular base portion at a second end thereof remote from said first end, said head assembly comprising (1) means for affixing a laryngoscope blade to the handle and permitting movement of the blade between a storage position which is substantially parallel to the handle and a working position which is substantially perpendicular to the handle; and (2) a lamp, said lamp being held in a position whereby the lamp is aligned with an optical fiber in the laryngoscope blade when the blade is in the working position; and (d) a switch assembly disposed within handle, said switch assembly acting to establish an electrical circuit between the lamp and a battery placed in the base portion when the laryngoscope blade is moved into the working position; wherein the switch assembly comprises:

(1) a first sleeve in which the lamp is mounted, said first sleeve providing electrical contact between a side terminal of the lamp and the tubular base portion and leaving a base terminal of the lamp exposed, and said first sleeve being axially slidable within the handle;

(2) a spring operative to press the first sleeve towards the head-end of the handle;

(3) an electrically insulating barrel mounted within the handle between the first sleeve and the first end of the base portion, said electrically insulating barrel having an axial channel therethrough, said axial channel having a bottom region of greater cross section at a bottom end directed toward the first end of the tubular base portion and a top region of smaller cross section at a top end directed toward the head;

(4) an electrically conductive sliding terminal, said sliding terminal being slidably disposed within the bottom region of the channel in the barrel; and (5) an electrically conductive plunger affixed to the sliding terminal and slidably disposed within the top region of the channel in the insulating barrel such that the sliding terminal and the plunger slide as a unit within the channel.

DETAILED DESCRIPTION OF THE INVENTION

Figure 1:
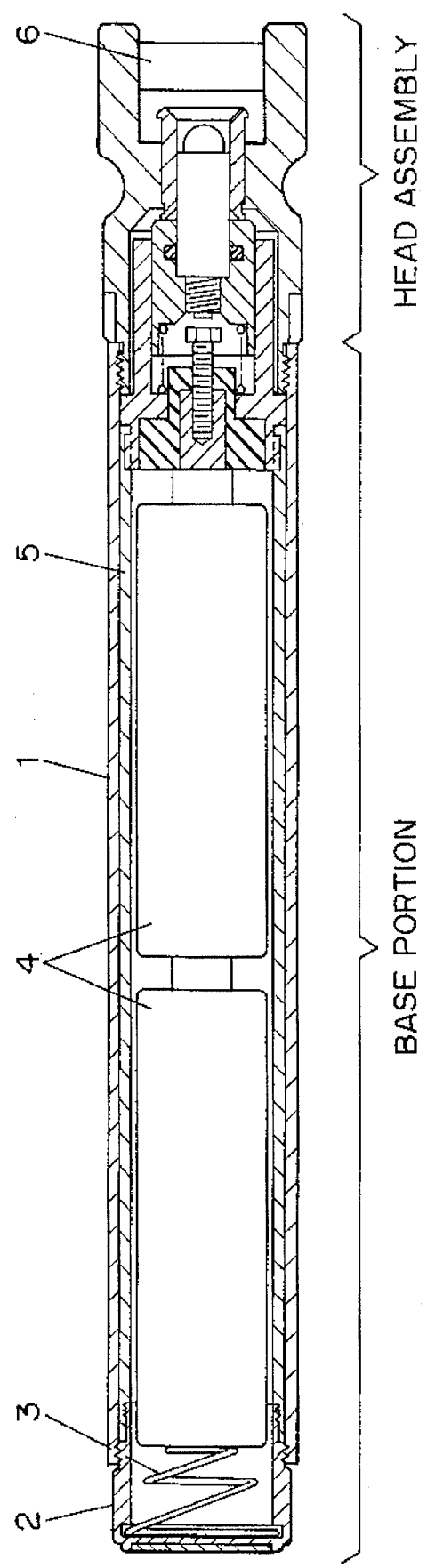
FIG. 1 shows a cross-section of a laryngoscope handle in accordance with the present invention.

As shown in FIG. 1, a laryngoscope handle in accordance with the invention is formed from a tubular base portion and a head assembly. The base portion can be formed as a single piece or from a separate housing 1 and bottom cap 2 as shown in FIG. 1. At the bottom end of the base portion is a first electrical contact 3 for making contact with batteries 4 disposed within the housing 1. In the embodiment shown in FIG. 1, a battery case 5 separates the batteries 4 from the housing 1.

Figure 5A:
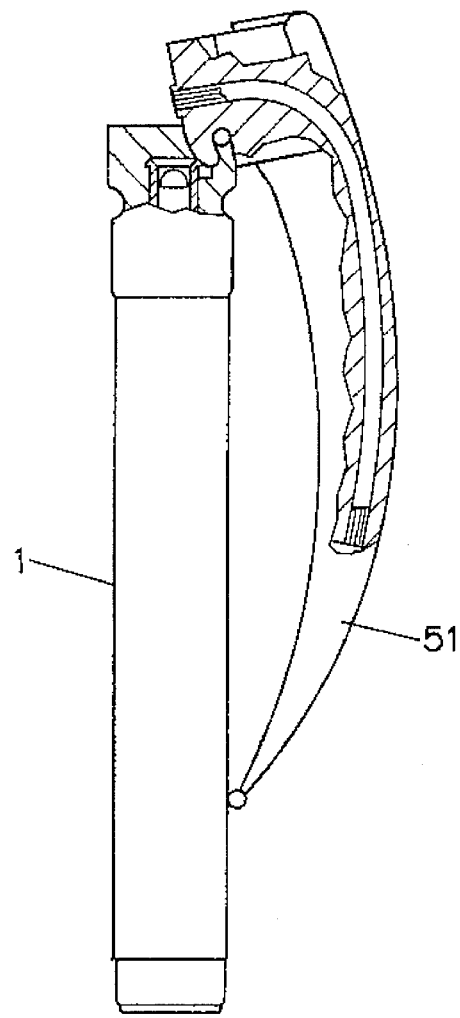
FIGS. 5A and 5B shows a handle according to the invention with the laryngoscope blade attached.
Figure 5B:
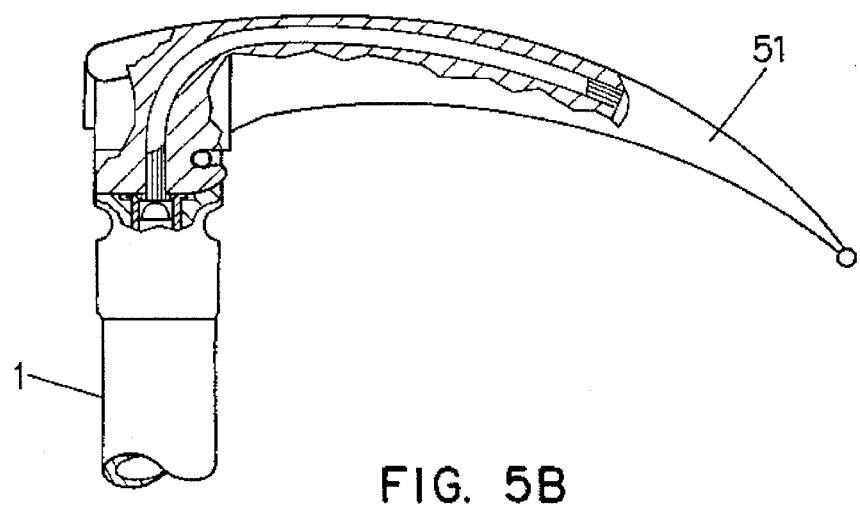

The head assembly is affixed to the top end of the base portion, preferably by way of a threaded coupling as shown in FIG. 1. The head assembly includes means for affixing a laryngoscope blade to the handle and permitting movement of the blade 51 between a storage position which is substantially parallel to the handle (FIG. 5A) and a working position which is substantially perpendicular to the handle (FIG. 5B). In FIG. 1 this is the pivot pin 6 which interacts with a hook on a laryngoscope blade in a manner known in the art, and permits the blade to pivot between the two positions.

Figure 2:
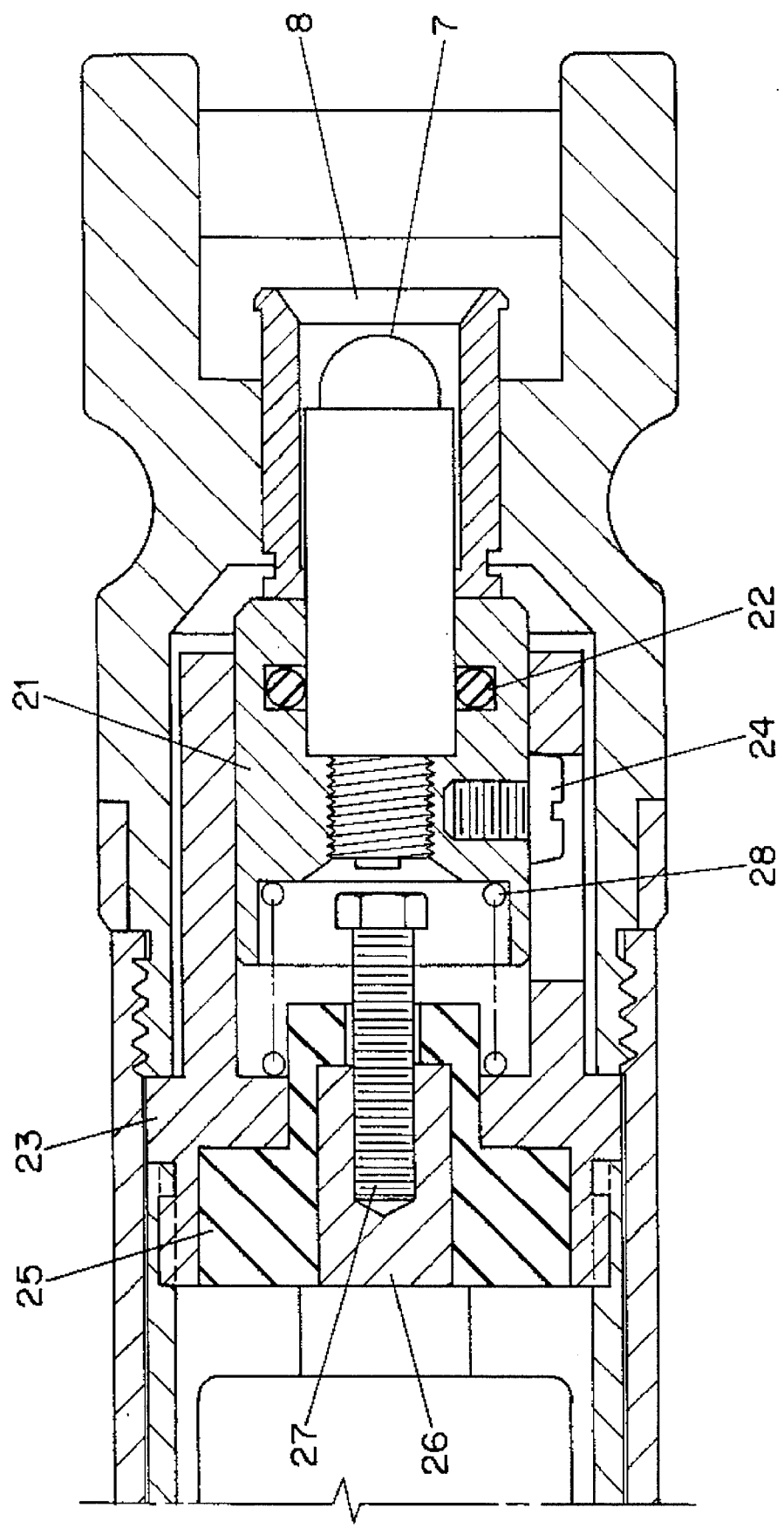
FIG. 2 shows a cross-section of a switch assembly in accordance with the present invention.

As shown in FIG. 2, the head assembly has a central bore which receives a lamp 7 and a sliding blade sleeve 8. The position of the bore is such that the blade sleeve 8 is pressed downward towards the base portion of the handle and the lamp 7 is in alignment with an optical fiber in the laryngoscope blade when the blade is in the working position.

Figure 3:
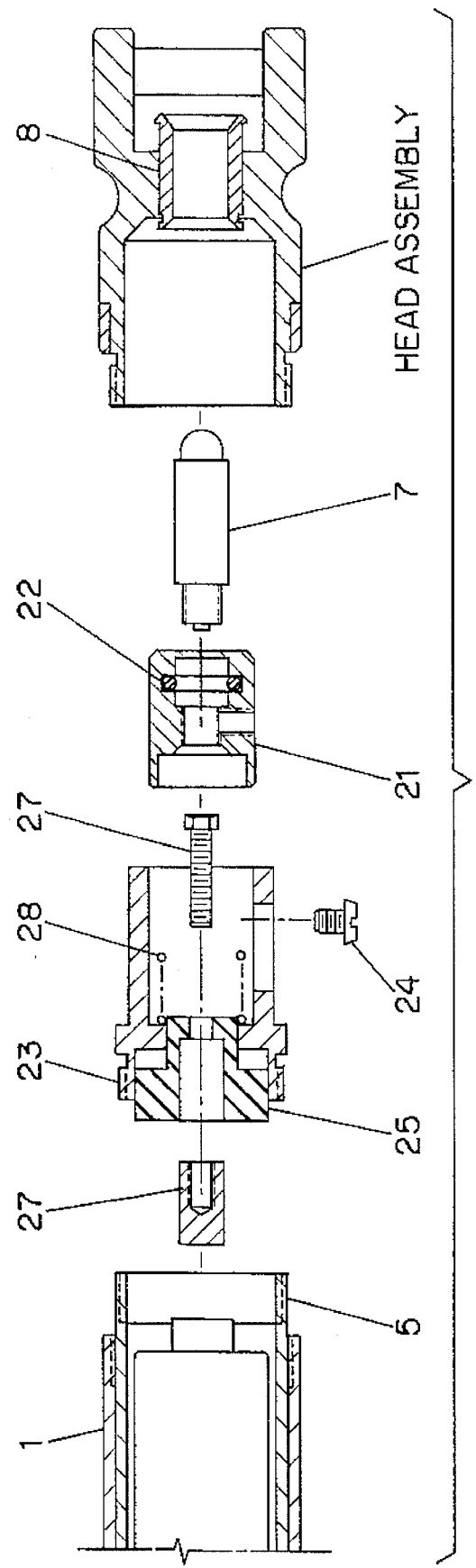
FIG. 3 shows the cross-section of the switch assembly in an exploded view.
Figure 4:
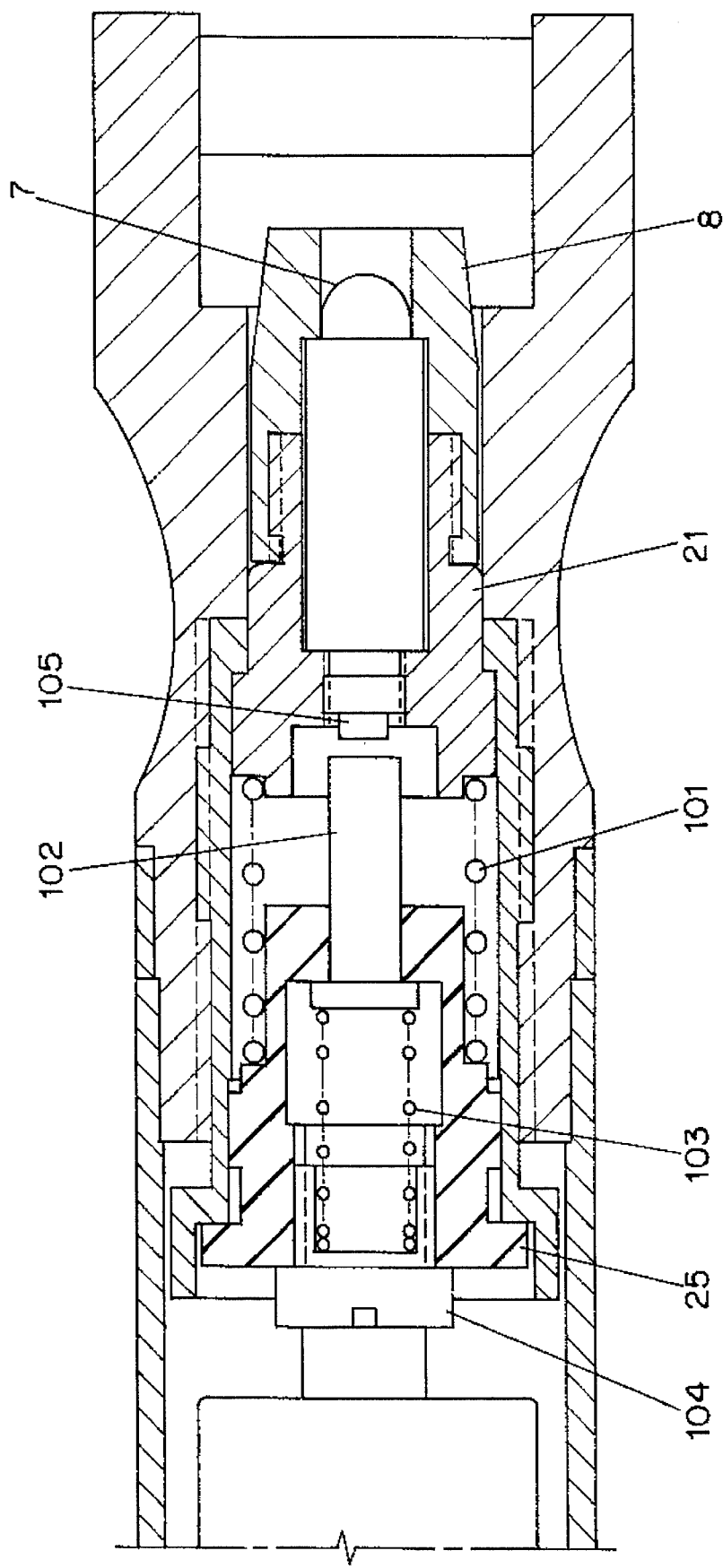
FIG. 4 shows a switch mechanism in accordance with a prior art design.

The switch assembly in accordance with the present invention is shown in greater detail in FIGS. 2 and 3, where like numbers are given to like parts. As shown, the lamp 7 is threaded into an opening-in electrically conductive mounting sleeve 21. An O-ring 22 is disposed within the mounting sleeve 21 to tension the lamp within the socket. The mounting sleeve 21 is placed inside a collar 23 which has a central opening sized to permit the mounting sleeve to slide axially within the handle while maintaining its lateral position. A screw 24 is inserted into the mounting sleeve 21 through an opening in the collar 23 such that the head of the screw 24 limits the extent to which the mounting sleeve can slide.

At the base of the collar is an electrically insulating barrel 25. The barrel 25 has an axial channel therethrough, said axial channel having a bottom region of greater cross section at the end directed toward the bottom of the handle and a top region of smaller cross section at a top end directed toward the head. The barrel accepts an electrically conductive sliding terminal 26 into the bottom region of the channel. An electrically conductive plunger 27 is inserted slidably within the top region of the channel in the barrel 25 and is affixed to the sliding terminal 26. For example, the plunger 27 may be affixed by threading it into an opening in the sliding terminal 26. Finally, a spring 28 is disposed in the space between the top of the collar 23 and the bottom of the mounting sleeve 21 such that the plunger 27 passes through the center of the spring.

The plunger 27 and the sliding terminal 26 slide as a unit in the channel within the insulating barrel. A cap at the top of the plunger prevents the unit from sliding out of the channel in a downward direction, while the reduction in the diameter of the channel defines the limit of the movement of the plunger toward the head end of the handle.

When the blade of the laryngoscope is moved into the working position, the blade sleeve 8 is depressed downwards. This in turn presses the mounting sleeve 21 down and brings the center contact of the lamp 7 into contact with the upper end of the plunger 27 at the same time that the sliding terminal is in contact with the upper terminal of a battery placed in the housing. This creates a complete electrical circuit which runs from the bottom of the batteries 4, through the electrical contact 3, the bottom cap 2, the housing 1, the body of the head assembly, the collar 23, the mounting sleeve 21, the shell of the lamp 7, the plunger 27 and the sliding terminal 26.

The switch assembly of the present invention provides the advantage of large, positive contact surfaces between the lamp terminal and the plunger on the one hand and the sliding terminal and the top terminal of the battery on the other. Moreover, because the position of the sliding terminal 26 relative to the housing can vary when the switch is activated, the tension holding the batteries in contact with the electrical contacts is dynamically increased when the switch is in the on position, but is reduced when the switch is off. This has the effect of decreasing extending the useful life of the handle without adjustment of the battery contacts to maintain well established electrical contacts.

While the device shown in FIGS. 1–3 represents a preferred embodiment of the present, invention, numerous variations will be apparent to the person skilled in the art without departing from the spirit and scope of the invention. For example, while the maximum travel of the mounting sleeve 21 is shown as being defined using a screw 24 as a detent means, the invention is not limited to the use of screws for this purpose. For example, an extension might be glued or welded to the side of the mounting sleeve 21 for this purpose. Moreover, it will be appreciated that the use of a detent means cooperating with an opening in the collar is not the only way to define the upper limit of travel of the mounting sleeve 21. Indeed, a flange attached to or extending from a portion of the head assembly might be used for this purpose.

I claim:

1. A laryngoscope handle comprising:
   (a) a tubular base portion,
   (b) a first electrical contact disposed within and at a first end of the tubular base portion for making contact with a battery placed within said base portion;
   (c) a head assembly attached to the tubular base portion at a second end thereof remote from said first end, said head assembly being disposed at a head-end of the handle and comprising:
      (1) means for affixing a laryngoscope blade to the handle and permitting movement of the blade between a storage position which is substantially parallel to the handle and a working position which is substantially perpendicular to the handle; and
      (2) a lamp having a base terminal and a side terminal, said lamp being held in a position whereby the lamp is aligned with an optical fiber in the laryngoscope blade when the blade is in the working position; and
   (d) a switch assembly disposed within said handle, said switch assembly acting to establish an electrical circuit between the lamp and a battery placed in the base portion when the laryngoscope blade is moved into the working position, wherein the switch assembly comprises:
      (1) a first sleeve in which the lamp is mounted, said first sleeve providing electrical contact between the side terminal of the lamp and the tubular base portion and leaving the base terminal of the lamp exposed, and said first sleeve being axially slidable within the handle;
      (2) a spring operative to press the first sleeve towards the head-end of the handle;
      (3) an electrically insulating barrel mounted within the handle between the first sleeve and the first end of the base portion, said electrically insulating barrel having an axial channel therethrough, said axial channel having a bottom region of greater cross section at a bottom end directed toward the first end of the tubular base portion and a top region of smaller cross section at a top end directed toward the head-end of the handle;
      (4) an electrically conductive sliding terminal, said sliding terminal being slidably disposed within the bottom region of the axial channel in the electrically conductive barrel; and
      (5) an electrically conductive plunger affixed to the sliding terminal and slidably disposed within the top region of the axial channel in the insulating barrel such that the sliding terminal and the plunger slide as a unit within the channel.

2. A laryngoscope handle according to claim 1, wherein the switch assembly further comprises an electrically conductive collar disposed within the handle and having an axial opening therein to receive the first sleeve.

3. A laryngoscope handle according to claim 2, wherein the collar has a side opening passing through one side thereof, further comprising detent means affixed to the first sleeve through said side opening in the collar to define the maximum extent to which the first sleeve can slide relative to the collar.

4. A laryngoscope handle according to claim 3, wherein the detent means is a screw.

5. A laryngoscope handle according to claim 1, wherein the electrically conductive plunger is threaded into a hole in the sliding terminal.

* * * * *